(12) United States Patent
Kaouas et al.

(10) Patent No.: US 8,816,102 B2
(45) Date of Patent: Aug. 26, 2014

(54) COMPOUNDS

(75) Inventors: Abdelmajid Kaouas, Utrecht (NL); Harry Renes, Lelystad (NL); Alexander P. Tondeur, Loosdrecht (NL); Cornelis Winkel, Bussum (NL)

(73) Assignee: Givaudan S.A., Vernier (CH)

( * ) Notice: Subject to any disclaimer, the term of this patent is extended or adjusted under 35 U.S.C. 154(b) by 250 days.

(21) Appl. No.: 13/378,257

(22) PCT Filed: Jun. 24, 2010

(86) PCT No.: PCT/EP2010/059027
§ 371 (c)(1),
(2), (4) Date: Dec. 14, 2011

(87) PCT Pub. No.: WO2010/149754
PCT Pub. Date: Dec. 29, 2010

(65) Prior Publication Data
US 2012/0093742 A1 Apr. 19, 2012

(30) Foreign Application Priority Data
Jun. 25, 2009 (GB) .................................. 0911000.8

(51) Int. Cl.
*C07D 317/44* (2006.01)
*A24B 15/30* (2006.01)
*A24B 15/36* (2006.01)
*A23L 1/226* (2006.01)
*C07D 317/60* (2006.01)
*C07C 235/34* (2006.01)
*C07C 235/78* (2006.01)

(52) U.S. Cl.
CPC ......... *A23L 1/22671* (2013.01); *A23L 1/22657* (2013.01); *C07D 317/60* (2013.01); *C07C 235/34* (2013.01); *C07C 235/78* (2013.01)
USPC ............................ 549/436; 131/276; 131/277

(58) Field of Classification Search
USPC .................................... 549/436; 131/276, 277
See application file for complete search history.

(56) References Cited

U.S. PATENT DOCUMENTS

| | | | |
|---|---|---|---|
| 5,387,714 A | 2/1995 | Takase et al. | |
| 2003/0171617 A1 | 9/2003 | Ley | |
| 2005/0208084 A1 | 9/2005 | Ley et al. | |
| 2008/0199584 A1 | 8/2008 | Kaouas et al. | |
| 2009/0169696 A1 | 7/2009 | Renes et al. | |

FOREIGN PATENT DOCUMENTS

| | | |
|---|---|---|
| EP | 0 535 928 A2 | 4/1993 |
| JP | 2006-176433 | 7/2006 |
| WO | WO 01/98258 * | 12/2001 |
| WO | WO 03/106404 A1 | 12/2003 |
| WO | WO 2005/102071 A1 | 11/2005 |
| WO | WO 2007/027095 A1 | 3/2007 |

OTHER PUBLICATIONS

Walpole et al, J. Med. Chem. vol. 36 pp. 2373-2380, (1993).*
Wood et al FEBS vol. 269 No. 2 pp. 381-385 (1990).*
PCT/EP2010/059027—Written Opinion of the International Searching Authority, Sep. 28, 2010.
PCT/EP2010/059027—International Search Report, Sep. 28, 2010.
GB 09 11 000.8—Great Britain Search Report, Aug. 28, 2009.
Ley, et al., "Pungency of Various Substituted Mandelic Acid Alkyl Amides", State-of-the-Art in Flavour Chemistry and Biology, Proceedings of the 7th Wartburg Symposium on Flavour Chemistry and Biology, 2004, pp. 68-74, CAS Abstract Accession. No. 2005:649867.

* cited by examiner

*Primary Examiner* — Andrew D Kosar
*Assistant Examiner* — Raymond Covington
(74) *Attorney, Agent, or Firm* — Curatolo Sidoti Co., LPA; Joseph G. Curatolo; Salvatore A. Sidoti

(57) ABSTRACT

A method of modulating the flavor of an orally-receivable product, such as a foodstuff, beverage, dentifrice or medicine, comprising the addition thereto of a flavor-modulating proportion of at least one compound of the formula I

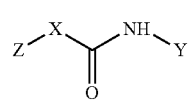

I in which
X is selected from CHOH, C=O, $CH_2$—CO and CH=C (OH),
Y is selected from C1-C7 linear and branched alkyl and $CH_2CH_2OH$,
Z is selected from $CH_3$ and a moiety of the formula II

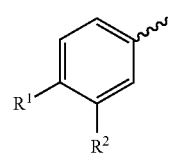

II in which the wavy bond represents bond linking Z to X and $R^1$ and $R^2$ are selected from the possibilities
(i) both hydrogen;
(ii) independently OH and $OCH_3$; and
(iii) $R^1$ and $R^2$ together with their bonds to the phenyl ring form a ring of the formula —O—$CH_2$—O—;
such that, when Z is $CH_3$, X is C=O and Y is $CH_2CH_2OH$.

10 Claims, No Drawings

COMPOUNDS

CROSS REFERENCE TO RELATED APPLICATIONS

This application is a national stage application of International Application No. PCT/EP2010/059027, filed 24 Jun. 2010, which claims priority from Great Britain Patent Application Serial No. 0911000.8, filed 25 Jun. 2009, from which applications priority is claimed, and which are incorporated herein by reference.

This disclosure relates to flavour modulation and to compounds for achieving this.

The modulation of flavour in orally-receivable compositions, such as foodstuffs, beverages, medicines, mouthwashes and the like, by the addition of edible substances to confer or modify flavour has become an important factor in the production of such compositions. The use of "modulation" in this description covers the cases of conferring flavour and modifying flavour. New flavours are constantly being sought. In addition, there is interest in the modification of existing flavours. This has become very important, especially the enhancement of salt, umami and sugar taste in health foods. Generally, this involves giving the impression that there is present more of a substance, typically salt, monosodium glutamate (MSG) or sugar, than there actually is. Thus, the quantities of the original materials can be reduced, with consequent important health and dietary benefits. In such cases, the quantity of edible substance added is generally so low that it cannot be tasted. The nature of this action is not completely understood.

It has now been found that a particular class of substances can have such a modulating effect on the flavour of an orally-receivable product. There is therefore provided a method of modulating the flavour of an orally-receivable product, comprising the addition thereto of a flavour-modulating proportion of at least one compound of the formula I

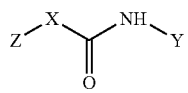

I in which
X is selected from CHOH, C=O, $CH_2$—CO and CH=C(OH),
Y is selected from C1-C7 linear and branched alkyl and $CH_2CH_2OH$,
Z is selected from $CH_3$ and a moiety of the formula II

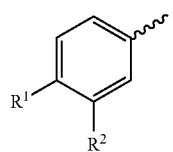

II in which the wavy bond represents bond linking Z to X and
$R^1$ and $R^2$ are selected from the possibilities
(i) both hydrogen;
(ii) independently OH and $OCH_3$; and
(iii) $R^1$ and $R^2$ together with their bonds to the phenyl ring form a ring of the formula —O—$CH_2$—O—;
such that, when Z is $CH_3$, X is C=O and Y is $CH_2CH_2OH$ Some of the compounds hereinabove mentioned are novel. There is therefore provided a compound of the formula I as hereinabove described, in which
X is selected from CHOH and C=O,
Y is selected from n-heptyl, heptan-4-yl and $CH_2CH_2OH$,
Z is a moiety of the formula II in which R1 and R2 are selected from one of the following:
(a) R1 is OH and R2 is OCH3;
(b) R1 is OCH3 and R2 is OH;
(c) $R^1$ and $R^2$ together with their bonds to the phenyl ring form a ring of the formula —O—$CH_2$—O—

Particular specific examples are
N-(2-hydroxyethyl)-2-oxo-2-phenylacetamide
2-(benzo[d][1,3]dioxol-5-yl)-N-(2-hydroxyethyl)-2-oxoacetamide
2-(benzo[d][1,3]dioxol-5-yl)-N-(heptan-4-yl)-2-oxoacetamide
N-(heptan-4-yl)-2-(4-hydroxy-3-methoxyphenyl)-2-oxoacetamide
N-heptyl-2-(4-hydroxy-3-methoxyphenyl)-2-oxoacetamide
N-(heptan-4-yl)-2-hydroxy-2-(4-hydroxy-3-methoxyphenyl)acetamide
N-heptyl-2-hydroxy-2-(4-hydroxy-3-methoxyphenyl)acetamide
N-heptyl-2-oxo-3-phenylpropanamide
N-(heptan-4-yl)-2-oxo-3-phenylpropanamide
N-(2-hydroxyethyl)-2-oxo-propanoyl amide The compounds can be prepared in several ways known by those skilled in the art. One of the typical methods involves reaction of the free acid with the corresponding amine in the presence of a coupling agent, typical examples are carbodiimides. Another method involves reaction of the ester with the desired amine in the presence of a base catalyst. This can be the amine itself. Reactions can be carried out without or with organic solvents. THF, 1,4-dixoane, dichloromethane or chloroform were preferred when the coupling reagents are used. When the alpha keto carboxylic esters are used reactions can be carried out without solvent or with solvent, ethanol being particularly suited.

Reaction temperature is dependent on the reactivity of the compounds but is between room temperature and 120° C.

It might sometimes be required to protect functional groups that would otherwise react under the chosen reaction conditions. Also it is possible that conversions need to take place after the amide bond is established. The skilled person will readily recognise when such protection is necessary.

The compounds may be incorporated by conventional means into orally-receivable compositions. Within the term "orally-receivable compositions" is included all compositions that are taken into the mouth for ingestion or for spitting out for any reason, be it for pleasure, nourishment or medicinal reasons. These include, but are not limited to foodstuffs, beverages, nutraceuticals and dental care products including mouth wash.

Food products include cereal products, rice products, pasta products, ravioli, tapioca products, sago products, baker's products, biscuit products, pastry products, bread products. confectionery products, dessert products, gums, chewing gums, chocolates, ices, honey products, treacle products, yeast products, salt and spice products, savory products, mustard products, vinegar products, sauces (condiments), processed foods, cooked fruits and vegetable products, meat and meat products, meat analogues/substitutes, jellies, jams, fruit sauces, egg products, milk and dairy products, cheese products, butter and butter substitute products, milk substitute products, soy products, edible oils and fat products, medicaments, food extracts, plant extracts, meat extracts, condiments, nutraceuticals, gelatins, tablets, lozenges, drops, emulsions, elixirs, syrups, and combinations thereof.

Other specific compositions include condiments and sauces (cold, warm, instant, preserved, sate, tomato, BBQ Sauce, Ketchup, mayonnaise and analogues, bechamel), gravy, chutney, salad dressings (shelf stable, refrigerated), batter mixes, vinegar, pizza, instant noodles, french fries, croutons, salty snacks (potato chips, crisps, nuts, tortilla-tostada, pretzels, cheese snacks, corn snacks, potato-snacks, ready-to-eat popcorn, microwaveable popcorn, caramel corn, pork rinds, nuts), crackers (Saltines, 'Ritz' type), "sandwich-type" cracker snacks, breakfast cereals, cheeses and cheese products including cheese analogues (reduced sodium cheese, pasteurized processed cheese (food, snacks & spreads), savoury spreads, cold pack cheese products, cheese sauce products), meats, aspic, cured meats (ham, bacon), luncheon/breakfast meats (hotdogs, cold cuts, sausage), soy-based products, tomato products, potato products, dry spice or seasoning compositions, liquid spice or seasoning compositions including pesto, marinades, and soup-type/meal-alternative beverages, and vegetable juices including tomato juice, carrot juice, mixed vegetable juices and other vegetable juices.

Beverages includes any liquid, available in liquid or dis-solvable form for consumption, and includes juices, fruit juices, vegetable juices, tea and tea-based drinks, coffee and coffee-based drinks, soft drinks and sodas, fermented and distilled alcoholic drinks, such as beer, lager, stout, wines, and flavoured alcoholic beverages, such as "alcopops".

Processed foods include margarine, peanut butter, soup (clear, canned, cream, instant, UHT), canned juices, canned vegetable juice, canned tomato juice, canned fruit juice, canned juice drinks, canned vegetables, pasta sauces, frozen entrees, frozen dinners, frozen hand-held entrees, dry packaged dinners (macaroni & cheese, dry dinners-add meat, dry salad/side dish mixes, dry dinners—with meat). Soups may be in different forms including condensed wet, ready-to-serve, ramen, dry, and bouillon, processed and pre-prepared low-sodium foods.

There is therefore also provided an orally-receivable product, comprising a product base and a compound of Formula I, as hereinabove defined. By "product base" is meant the totality of all the standard ingredients of the particular orally-receivable product in question, used in art-recognised quantities. It will be understood that there may be used more than one compound of Formula I, and that the use of the singular "a compound" does not limit the composition to one such compound.

The concentration used will depend on the particular composition and the desired nature of the modulation. The skilled person can readily determine a suitable concentration in every case, but as a non-limiting, general indication, the concentration lies between 0.1 and 100 ppm. In the case of use as a flavourant, typical concentrations will be between 5 and 100 ppm whereas typical concentrations for flavour modification will be between 0.1 and 10 ppm There is therefore also provided
(a) a method of flavouring an orally-receivable product, comprising the addition thereto of from 0.1 to 100 ppm. of a compound of Formula I, as hereinabove defined; and
(b) a method of modifying the flavour of a flavourant-containing orally receivable product, comprising the addition thereto of from 0.1-10 ppm of a compound of Formula I, as hereinabove defined.

The method is now further described with reference to the following examples, which exemplify particular embodiments and which are not intended to be in any way limiting.

EXAMPLE 1

Preparation of N-(2-hydroxyethyl)-2-oxo-2-phenylacetamide

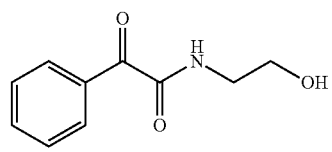 [SMILES: O=C(NCCO)C(=O)c1ccccc1]

EDCl (1-(3-dimethylaminopropyl)-3-ethylcarbodiimide hydrochloride) (3 g, 15.6 mmol) and HOBt (1-hydroxybenzotriazole) (0.2 g, 1.5 mmol) were added to a stirred and cooled (0° C.) solution of phenylglyoxylic acid (2 g, 13.3 mmol) in DCM (50 ml). The resulting reaction mixture was cooled to −5° C. and then ethanolamine (2 g, 32.8 mmol) was added dropwise at reaction temperature below 0° C. Upon the addition, the resulting suspension was stirred for 1 hour at temperature below 0° C. and then at room temperature overnight. The reaction mixture was poured into 1% aqueous hydrochloric acid solution (30 ml). The DCM phase was washed with water and concentrated in vacuum.

The crude product was chromatographed on a silica gel column using ethylacetate/hexane (1:2) as eluent to provide the title compound (0.5 g, 19.5% yield) as yellow oil.

$^1$H-NMR in DMSO-d6: 3.207-3.430 (2H, m, NH—CH2-CH2), 3.449-3.591 (2H, m, CH2-CH2-OH), 4.565 (1H, s, OH), 7.500-8.071 (5H, 3×m, 5× aromatic H), 8.715-9.050 (1H, s, NH)

EXAMPLE 2

Preparation of 2-(benzo[d][1.3]dioxol-5-yl)-N-(2-hydroxyethyl)-2-oxoacetamide

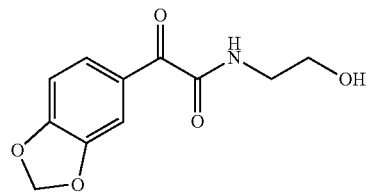 [SMILES: O=C(NCCO)C(=O)c1ccc2c(c1)OCO2]

Ethanolamine (3.5 g, 49 mmol) was added to a stirred solution of benzo[1,3]dioxol-5-yl-oxo-acetic acid ethyl ester (2.5 g, 11 mmol)) in ethanol (40 ml)) at room temperature. The resulting reaction mixture was heated to reflux for 2 hours. Then ethanol was distilled off and stirring was continued at 120° C. for 1 hour. The reaction mixture was cooled to room temperature and then 50 ml of THF and 100 ml of aqueous HCl solution were added and stirred for 30 minutes. The mixture was extracted twice with DCM (50 ml). The organic layer was washed twice with water (50 ml) and evaporated to provide a dark sticky product. The product was further crystallized in pentane/ethyl acetate. Red crystals of the title compound (0.9 g, 34.5% yield) were obtained.

¹H-NMR in CDCl3: 3.207-3.430 (2H, m, NH—CH2-CH2), 3.449-3.591 (2H, m, CH2-CH2-OH), 4.565 (1H, s, OH), 5.98-6.14 (2H, s, —O—CH2-O), 6.73-8.27 (3H, 3×m, aromatic H), 7.72-7.67 (1H, s, NH)

EXAMPLE 3

Preparation of 2-(benzo[d][1,3]dioxol-5-yl)-N-(heptan-4-yl)-2-oxoacetamide

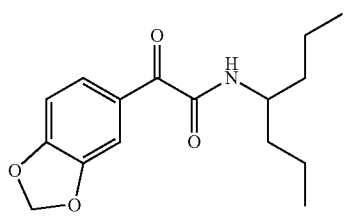 [SMILES: CCCC(CCC)NC(=O)C(=O)c1ccc2c(c1)OCO2]

4-Heptylamine (2.5 g, 22 mmol) was added to a stirred solution of benzo[1,3]dioxol-5-yl-oxo-acetic acid ethyl ester (2 g, 9 mmol)) in ethanol (40 ml)) at room temperature. The resulting reaction mixture was heated to reflux for 4 hours. Then ethanol was distilled off and stirring was continued at 110° C. for 2 hours. The reaction mixture was cooled to room temperature and then 50 ml of THF and 100 ml of aqueous HCl solution were added and stirred for 30 minutes. The mixture was extracted twice with DCM (50 ml). The organic layer was washed twice with water (50 ml) and concentrated in vacuum. The crude product was chromatographed on a silica gel column using ethylacetate/heptane (2:3) as eluent to provide the title compound (0.5 g, 29% yield) as red crystals.

¹H-NMR in CDCl3: 0.93 (6H, t, 2×-CH2-CH3), 1.183-1.547 (8H, m, 2×C—CH2-CH2-CH3), 4.00 (1H, m, CONH—CH), 6.07 (2H, s, —O—CH2-O), 6.82 (1H, d, NH), 6.8508.25 (3H, d, s, d, aromatic H)

EXAMPLE 4

Preparation of N-(heptan-4-yl)-2-(4-hydroxy-3-methoxyphenyl)-2-oxoacetamide

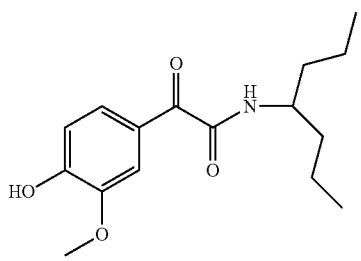 [SMILES: CCCC(CCC)NC(=O)C(=O)c1ccc(O)c(OC)c1]

N-(heptan-4-yl)-2-(4-hydroxy-3-methoxyphenyl)-2-oxoacetamide was prepared from 4-hydroxy-3-methoxy-phenyl)-oxo-acetic acid ethyl ester and 4-heptylamine by the same procedure described for the preparation of 2-(benzo[d][1,3]dioxol-5-yl)-N-(heptan-4-yl)-2-oxoacetamide. White crystals of the title compound (0.7 g, 34% yield) were obtained.

¹H-NMR in DMSO-6d: 0.88 (6H, t, 2×-CH2-CH3), 1.183-1.547 (8H, m, 2×C—CH2-CH2-CH3), 3.80 (3H, s, CH3-O—Ar), 3.90 (1H, m, CONH—CH), 6.77-7.50 (3H, m, aromatic H), 8.47 (1H, s, CONH), 8.87 (1H, s, phenolic OH)

EXAMPLE 5

Preparation of N-heptyl-2-(4-hydroxy-3-methoxyphenyl)-2-oxoacetamide

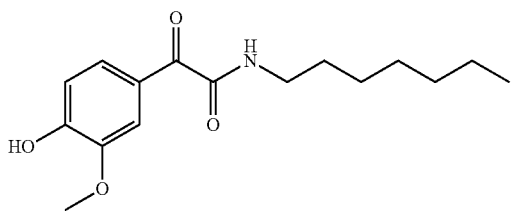 [SMILES: CCCCCCCNC(=O)C(=O)c1ccc(O)c(OC)c1]

Manganese oxide 60% (4.5 g, 31 mmol) was added to a stirred solution of N-heptyl-2-hydroxy-2-(4-hydroxy-3-methoxy-phenyl)-acetamide (0.5 g, 1.7 mmol) in chloroform (50 ml) at room temperature. The resulting mixture was stirred at room temperature for 24 hrs. filtered, and centrifuged to remove the remaining of manganese oxide. The filtrate was concentrated in vacuum. The crude product was chromatographed on a silica gel column using ethyl acetate/heptane (2:3) as eluent to provide the title compound (0.15 g, 30% yield) as pale yellow crystals.

¹H-NMR in DMSO-6d: 0.84 (3H, t, CH2-CH3), 1.04-1.49 (10H, m, NH—CH2(CH2)₅CH3), 2.89-3.17 (2H, m, CONH—CH2), 3.80 (3H, s, CH3-O—Ar), 6.77-7.50 (3H, m, aromatic H), 8.87 (1H, s, phenolic OH), 7.73-7.99 (1H, m, NH),

EXAMPLE 6

Preparation of N-(2-hydroxyethyl)-2-oxopropanamide

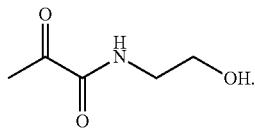

Ethanolamine (16 g, 66 mmol) was added dropwise to stirred ethyl pyruvate (8 g, 69 mmol) at temperature between 22 and 48° C. Then the mixture was heated to 120° C. and stirred at this temperature for 3 hours. During the reaction, the formed ethanol and water were removed by distillation. The reaction mixture was cooled to room temperature and poured into 40 ml of water. The mixture was acidified to pH<1 and stirred for 30 minutes at room temperature. The solution was saturated with sodium chloride and extracted with ethyl acetate a few times. The ethyl acetate layer was evaporated to dryness. The remaining residual oil was purified by silica gel column chromatography using heptane/ethyl acetate to yield colorless oil (1 g, 9% yield).

¹H-NMR in DMSO-d6: 2.25-2.35 (3H, s, CH3-CO), 3.1-3.3 (2H, m, NH—CH2-CH2), 3.4-3.51 (2H, m, CH2-CH2-OH), 4.6-4.8 (1H, s, OH), 8.-8.5 (1H, s, NH)

EXAMPLE 7

Preparation of N-(heptan-4-yl)-2-hydroxy-2-(4-hydroxy-3-methoxyphenyl)acetamide

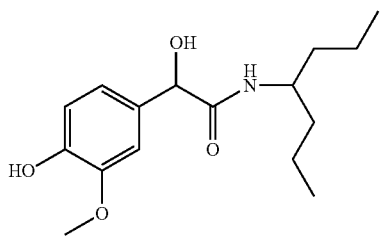 [SMILES: CCCC(CCC)NC(=O)C(O)c1ccc(O)c(OC)c1]

A solution of dicyclohexyl carbodiimide (DCC) (5.5 g, 26.7 mmol) in 1,4-dioxane (50 ml) was added to a stirred solution of 4-hydroxy-3-methoxymandelic acid (5 g, 25.3 mmol) and N-hydroxysuccinimide (3 g, 26.1 mmol) in 1,4-dioxane (100 ml) at room temperature. The resulting white suspension was stirred at room temperature for 16 hours. Then the reaction mixture was filtered. The filtrate was poured into a stirred solution of 4-heptylamine in water (20 ml) and sodium bicarbonate (2.5 g, 20 mmol) was added. The resulting solution was heated to 50° C. and stirred at this temperature for 1.5 hour. The cooled solution was acidified to pH<2 using aq. HCl 5% solution and extracted three times with ethyl acetate (100 ml). The combined organic layers were washed with brine, dried with sodium sulfate, filtered and the filtrate concentrated by evaporation under reduced pressure. The residue was purified by crystallization from ethyl acetate/heptane to yield the title product (5.5 g, 73.6%) as white crystals.

¹H-NMR in DMSO-6d: 0.76-0.82 (6H, m, 2×-CH2-CH3), 1.11-1.43 (8H, m, 2×C—CH2-CH2-CH3), 3.69 (1H, m, CONH—CH), 3.72 (3H, s, CH3-O—Ar), 4.75 (1H, s, CHOH—CONH), 5.9 (1H, d, CHOHCONH), 6.69-7.02 (3H, m, aromatic H), 8.46 (1H, d, NH), 8.95 (1H, s, phenolic OH)

EXAMPLE 8

Preparation of N-heptyl-2-hydroxy-2-(4-hydroxy-3-methoxyphenyl)acetamide

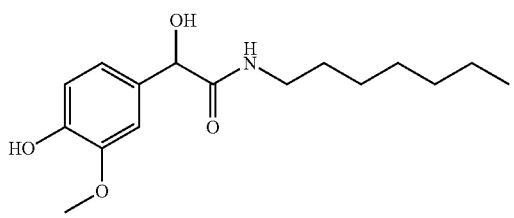 [SMILES: CCCCCCCNC(=O)C(O)c1ccc(O)c(OC)c1]

N-heptyl-2-hydroxy-2-(4-hydroxy-3-methoxyphenyl)acetamide was prepared from 4-hydroxy-3-methoxymandelic acid and n-heptylamine by the same procedure described for the preparation of N-(heptan-4-yl)-2-hydroxy-2-(4-hydroxy-3-methoxyphenyl)acetamide. White crystals of the title compound (6.7 g, 89% yield) were obtained.

¹H-NMR in DMSO-6d: 0.84 (3H, t, CH2-CH3), 1.04-1.49 (10H, m, NH—CH2(CH2)₅CH3), 2.89-3.17 (2H, m, CONH—CH2), 3.35 (1H, s, CHOH—CONH), 3.73 (3H, s, CH3-O—Ar), 4.75 (1H, s, CHOH—CONH), 5.9 (1H, d, CHOHCONH), 6.69-7.02 (3H, m, aromatic H), 7.87 (1H, m. NH), 8.87 (1H, s, phenolic OH)

EXAMPLE 9

N-heptyl-2-oxo-3-phenylpropanamide

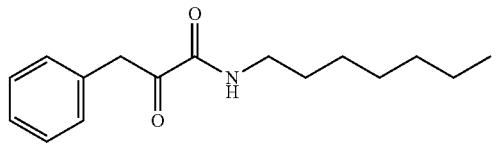 [SMILES: CCCCCCCNC(=O)C(=O)Cc1ccccc1]

A suspension of phenylpyruvic acid (2.1 g; 12.8 mmol) in DCM (50 ml) was cooled to 0° C. Then EDCl (3 g, 15.6 mmol) and HOBt (0.2 g, 1.5 mmol) were added successively. The resulted solution was cooled to −5° C. and then heptylamine (1.5 g, 13 mmol) was added dropwise at temperature below 0° C. Upon the addition the ice bath was removed and the reaction mixture was stirred overnight at room temperature. The reaction mixture was poured into 1% aqueous hydrochloric acid solution (30 ml). The DCM phase was washed with water and concentrated in vacuum. The crude product was chromatographed on a silica gel column using ethylacetate/hexane (1:2) as eluent to provide the title compound (0.8 g, 24% yield).

¹H-NMR in DMSO-6d: 0.84 (3H, t, CH2-CH3), 1.04-1.49 (10H, m, NH—CH2(CH2)₅CH3), 2.89-3.17 (2H, m, CONH—CH2), 3.5-4.0 (2H, s, CO—CH2-Ar), 7.500-8.071 (5H, 3×m, 5× aromatic H), 7.73-7.99 (1H, m, NH)

EXAMPLE 10

N-(heptan-4-yl)-2-oxo-3-phenylpropanamide

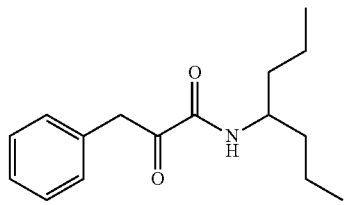 [SMILES: CCCC(CCC)NC(=O)C(=O)Cc1ccccc1]

A solution of DCC (2.8 g) in 1,4-dioxane (10 ml) was added to a solution of phenylpyruvic acid (2 g) and N-hydroxysuccinimide (1.5 g) in 1,4-dioxane (50) at rt. The resulting yellow suspension was stirred at rt for 18 hrs. Then the reaction mixture was filtered. The filtrate was poured into a solution of 4-heptylamine in water (20 ml) and then NaHCO3 (1.2 g) was added. The resulting reaction mixture was stirred for 2.5 hrs at 50° C., then cooled to rt and brought to pH<2 using aq. HCl 5% solution. Ethyl acetate was added (100 ml) and then the organic layer was separated washed twice with brine (50 ml) and concentrated by evaporation under reduced pressure. The residue was dissolved in ethyl acetate/heptane and placed in the refrigerator overnight. The crude product was purified by flash column chromatography (silica gel; ethyl acetate/heptane) to provide the title compound (0.5 g, 16% yield) as yellow solid.

$^1$H-NMR in DMSO-d6: 0.76-0.82 (6H, m, 2×-CH2-CH3), 1.11-1.43 (8H, m, 2×C—CH2-CH2-CH3), 3.69 (1H, m, CONH—CH), 3.5-4.0 (2H, s, CO—CH2-Ar), 7.500-8.071 (5H, 3×m. 5× aromatic H), 6.0-6.5 (1H, d, NH)

EXAMPLE 11

Testing of Compounds

EXAMPLE 11A

Two solutions were prepared:
A a solution of 0.3% NaCl
B a solution of 0.3% NaCl and 10 ppm Example 1 compound
The samples were tasted by a trained sensory panel composed of 20 women aged between 30 and 60.
Solution A: salty
Solution B: more salty, salivating

EXAMPLE 11B

Two solutions were prepared:
A a solution of 0.3% NaCl
B a solution of 0.3% NaCl and 10 ppm Example 5 compound.
The samples were tasted by a trained sensory panel composed of 20 women aged between 30 and 60.
Solution A: salty
Solution B: more salty, salivating, lingering

EXAMPLE 11C

Two solutions were prepared:
A a solution of 0.3% NaCl and 0.03% MSG
B a solution of 0.3% NaCl and 0.03% MSG and 10 ppm Example 6 compound.
The samples were tasted by a trained sensory panel composed of 20 women aged between 30 and 60.
Solution A: salty, umami
Solution B: more salty, more umami

EXAMPLE 11D

Two solutions were prepared:
A a solution of 0.3% NaCl, 0.03% MSG
B a solution of 0.3% NaCl, 0.03% MSG and 10 ppm N-heptyl-2-oxo-3-phenylpropionamide as prepared in example 9.
The samples were tasted by a trained sensory panel composed of 20 women aged between 30 and 60.
Solution A: salty, umami
Solution B: salty, stronger umami, more bouillon-like

EXAMPLE 11E

Two solutions were prepared:
A a solution of 0.3% NaCl and 0.03% MSG
B a solution of 0.3% NaCl, 0.03% MSG and 1 ppm N-(4-heptyl)-2-oxo-3-phenylpropionamide as prepared in example 10.
The samples were tasted by a trained sensory panel composed of 20 women aged between 30 and 60.
Solution A: salty, umami
Solution B: salty, more umami, more bouillon-like, slightly tingling.

EXAMPLE 11F

Two solutions were prepared:
A a solution of 0.3% NaCl and 0.03% MSG
B a solution of 0.3% NaCl, 0.03% MSG and 1 ppm N-heptyl 3-methoxy-4-hydroxy-mandelic acid as prepared in Example 8.
The samples were tasted by a trained sensory panel composed of 20 women aged between 30 and 60.
Solution A: salty, umami
Solution B: salty, more umami, slightly pungent.

EXAMPLE 12

Use in Tomato Soup

A tomato soup mix was prepared from 9.4 g of sodium chloride, 1 g of mono sodium glutamate, 0.08 g ribonucleotides (ex yeast), 32 g of tomato powder (ex Spreda), 25.1 g of glucose, 21 g of starch (Ultrasperse 5 ex National Starch), 5 g of palm fat powder, 3 g of yeast powder, 1 g on onion powder, 0.15 g of carrot powder, 0.05 g of ground white pepper, 0.3 g celery extract powder, 0.05 g of ground laurel leaf powder, and 1.85 g of sucrose. 25 G of the well mixed ingredients was added to 250 g of boiling water and stirred until completely dissolved.

The reference soup was compared with a batch of the same soup containing 10 ppm of N-(2-hydroxyethyl)-2-(benzo[1,3]dioxol-5-yl)-2-oxoacetamide as prepared in example 2. A small group of flavourists (2 male, 2 female) tasted the soups and agreed that the test soup was more umami, was more lingering and was more complex than the base soup.

EXAMPLE 13

Use in Potato Chips

Plain potato chips were prepared.
One part was flavoured with 1.2% sodium chloride (sample A)
One part was flavoured with 1.2% sodium chloride and 0.3% MSG (sample b)
One part was flavoured with 1.2% sodium chloride and 2.5 ppm N-(4-heptyl)-2-(benzo[1,3]dioxol-5-yl)-2-oxo-acetamide as prepared in example 3 (sample C).
The samples were tasted by a trained sensory panel composed of 20 women aged between 30 and 60.
The panel agreed that sample C was preferred over the other two samples. Sample A was described as salty, sample B as salty and umami and sample C as salty, umami, long lasting, savoury, bouillon. A slight bitter off-note was also observed in sample
C.

EXAMPLE 14

Use in Tomato Ketchup

A tomato ketchup was prepared from 19% tomato paste (28-30% dry weight), 8% of vinegar (15%), 3% of sodium chloride, 20% of sugar and 50% of water.

To one half of the batch was added 2 ppm of N-(4-heptyl) 2-(4-hydroxy-3-methyxophenol)-2-oxoacetamide (Example 5)

A small group of flavourists (2 male, 2 female) tasted the ketchups and agreed that the test ketchup tasted clearly more umami, more sweet and more full/complex compared with the base ketchup.

EXAMPLE 15

Further Use in Tomato Ketchup

A batch of tomato ketchup was prepared as described in Example 12. To one half of the batch was added 20 ppm N-(4-hepthyl) 4-hydroxy-3-methoxy-mandelic amide as prepared in Example 7.

A small group of flavourists (2 male, 2 female) tasted the ketchups and agreed that the test ketchup tasted more umami, more bouillon-like and more full/complex compared with the base ketchup.

The invention claimed is:

1. A method of modulating the flavour of an orally-receivable product, comprising the addition thereto of a flavour-modulating proportion of at least one compound of formula I

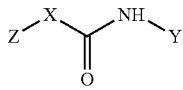

in which
X is selected from C=O, CH$_2$—CO and CH=C(OH),
Y is selected from C1-C7 linear and branched alkyl and CH$_2$CH$_2$OH,
Z is selected from CH$_3$ and a moiety of formula II

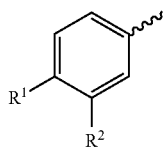

in which the wavy bond represents bond linking Z to X and R$^1$ and R$^2$ are selected from the possibilities
(i) both hydrogen;
(ii) independently OH and OCH$_3$; and
(iii) R$^1$ and R$^2$ together with their bonds to the phenyl ring form a ring of the formula —O—CH$_2$—O—;
such that, when Z is CH$_3$, X is C=O and Y is CH$_2$CH$_2$OH.

2. A method according to claim 1, in which the compound of formula I is selected from the group consisting of:
N-(2-hydroxyethyl)-2-oxo-2-phenylacetamide;
2-(benzo[d][1,3]dioxol-5-yl)-N-(2-hydroxyethyl)-2-oxoacetamide;
2-(benzo[d][1,3]dioxol-5-yl)-N-(heptan-4-yl)-2-oxoacetamide;
N-(heptan-4-yl)-2-(4-hydroxy-3-methoxyphenyl)-2-oxoacetamide;
N-heptyl-2-(4-hydroxy-3-methoxyphenyl)-2-oxoacetamide;
N-heptyl-2-oxo-3-phenylpropanamide;
N-(heptan-4-yl)-2-oxo-3-phenylpropanamide; and,
N-(2-hydroxyethyl)-2-oxo-propanoyl amide.

3. An orally-receivable product comprising a product base and a compound of Formula I

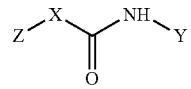

in which
X is selected from C=O, CH$_2$—CO and CH=C(OH),
Y is selected from C1-C7 linear and branched alkyl and CH$_2$CH$_2$OH,
Z is selected from CH$_3$ and a moiety of Formula II

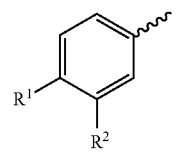

in which the wavy bond represents bond linking Z to X and R$^1$ and R$^2$ are selected from the possibilities
(i) both hydrogen;
(ii) independently OH and OCH$_3$; and
(iii) R$^1$ and R$^2$ together with their bonds to the phenyl ring form a ring of the formula —O—CH$_2$—O—;
such that, when Z is CH$_3$, X is C=O and Y is CH$_2$CH$_2$OH.

4. The orally-receivable product according to claim 3, in which the concentration of the compound of Formula I is from 0.1 to 100 ppm.

5. A method of flavouring an orally-receivable product, comprising the addition thereto of from 0.1 to 100 ppm of a compound of Formula I,

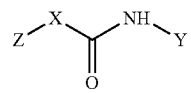

in which
X is selected from C=O, CH$_2$—CO and CH=C(OH),
Y is selected from C1-C7 linear and branched alkyl and CH$_2$CH$_2$OH,
Z is selected from CH$_3$ and a moiety of Formula II

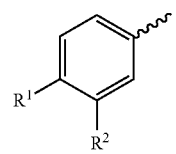

in which the wavy bond represents bond linking Z to X and R$^1$ and R$^2$ are selected from the possibilities
(i) both hydrogen;
(ii) independently OH and OCH$_3$; and
(iii) R$^1$ and R$^2$ together with their bonds to the phenyl ring form a ring of
the formula —O—CH$_2$—O—;

such that, when Z is CH₃, X is C=O and Y is CH₂CH₂OH.

6. A method of modifying the flavour of a flavourant-containing orally receivable product, comprising the addition thereto of from 0.1-10 ppm of a compound of Formula I,

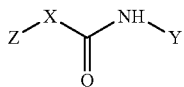
I in which
X is selected from C=O, CH₂—CO and CH=C(OH),
Y is selected from C1-C7 linear and branched alkyl and CH₂CH₂OH,
Z is selected from CH₃ and a moiety of Formula II

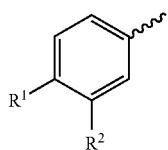
II in which the wavy bond represents bond linking Z to X and R¹ and R² are selected from the possibilities
(i) both hydrogen;
(ii) independently OH and OCH₃; and
(iii) R¹ and R² together with their bonds to the phenyl ring form a ring of the formula —O—CH₂—O—;
such that, when Z is CH₃, X is C=O and Y is CH₂CH₂OH.

7. A compound of formula I,

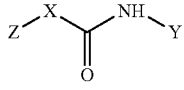
I in which
X is C=O,
Y is selected from n-heptyl, heptan-4-yl and CH₂CH₂OH,
Z is a moiety of formula II

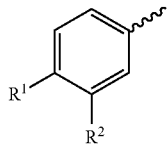
II in which R¹ and R² are selected from one of the following:
(a) R¹ is OH and R² is OCH₃;
(b) R¹ is OCH₃ and R² is OH;
(c) R¹ and R² together with their bonds to the phenyl ring form a ring of the formula —O—CH₂—O—.

8. The orally-receivable product according to claim 3, in which the compound of Formula I is selected from the group consisting of:
N-(2-hydroxyethyl)-2-oxo-2-phenylacetamide;
2-(benzo[d][1,3]dioxol-5-yl)-N-(2-hydroxyethyl)-2-oxoacetamide;
2-(benzo[d][1,3]dioxol-5-yl)-N-(heptan-4-yl)-2-oxoacetamide;
N-(heptan-4-yl)-2-(4-hydroxy-3-methoxyphenyl)-2-oxoacetamide;
N-heptyl-2-(4-hydroxy-3-methoxyphenyl)-2-oxoacetamide;
N-heptyl-2-oxo-3-phenylpropanamide;
N-(heptan-4-yl)-2-oxo-3-phenylpropanamide; and,
N-(2-hydroxyethyl)-2-oxo-propanoyl amide.

9. The method according to claim 5, in which the compound of Formula I is selected from the group consisting of:
N-(2-hydroxyethyl)-2-oxo-2-phenylacetamide;
2-(benzo[d][1,3]dioxol-5-yl)-N-(2-hydroxyethyl)-2-oxoacetamide;
2-(benzo[d][1,3]dioxol-5-yl)-N-(heptan-4-yl)-2-oxoacetamide;
N-(heptan-4-yl)-2-(4-hydroxy-3-methoxyphenyl)-2-oxoacetamide;
N-heptyl-2-(4-hydroxy-3-methoxyphenyl)-2-oxoacetamide;
N-heptyl-2-oxo-3-phenylpropanamide;
N-(heptan-4-yl)-2-oxo-3-phenylpropanamide; and,
N-(2-hydroxyethyl)-2-oxo-propanoyl amide.

10. The method according to claim 6 in which the compound of Formula I is selected from the group consisting of:
N-(2-hydroxyethyl)-2-oxo-2-phenylacetamide;
2-(benzo[d][1,3]dioxol-5-yl)-N-(2-hydroxyethyl)-2-oxoacetamide;
2-(benzo[d][1,3]dioxol-5-yl)-N-(heptan-4-yl)-2-oxoacetamide;
N-(heptan-4-yl)-2-(4-hydroxy-3-methoxyphenyl)-2-oxoacetamide;
N-heptyl-2-(4-hydroxy-3-methoxyphenyl)-2-oxoacetamide;
N-heptyl-2-oxo-3-phenylpropanamide;
N-(heptan-4-yl)-2-oxo-3-phenylpropanamide; and,
N-(2-hydroxyethyl)-2-oxo-propanoyl amide.

\* \* \* \* \*